United States Patent [19]

Takasugi

[11] Patent Number: 4,738,379
[45] Date of Patent: Apr. 19, 1988

[54] CARTRIDGE AND ITS EXTRACTOR

[75] Inventor: Mitsuo Takasugi, Kanagawa, Japan

[73] Assignee: Colpo Co., Ltd., Tokyo, Japan

[21] Appl. No.: 864,741

[22] Filed: May 13, 1986

Related U.S. Application Data

[63] Continuation of Ser. No. 704,883, Feb. 25, 1985, abandoned, which is a continuation of Ser. No. 480,239, Mar. 29, 1983, abandoned.

[30] Foreign Application Priority Data

Mar. 29, 1982 [JP] Japan .................................. 57-50790
Nov. 29, 1982 [JP] Japan ................................ 57-209122
Jan. 24, 1983 [JP] Japan .................................... 58-9494

[51] Int. Cl.⁴ .............................................. B65D 35/28
[52] U.S. Cl. .................................. 222/95; 222/327; 222/386.5; 222/575; 141/24; 604/191; 604/232
[58] Field of Search ............................ 222/135–137, 222/575, 95, 102, 214, 326, 327, 386.5, 325; 141/24, 27; 604/191, 212, 214, 216, 228, 232

[56] References Cited

U.S. PATENT DOCUMENTS

| | | | |
|---|---|---|---|
| 603,045 | 4/1898 | Palmer | 222/95 |
| 913,297 | 2/1969 | Krautschneider | 222/95 |
| 1,126,996 | 2/1915 | Hassler | 222/575 |
| 1,584,838 | 5/1926 | Brust | 222/575 |
| 1,704,921 | 3/1929 | Nicoll | 604/232 |
| 2,318,928 | 5/1943 | Deighton | 222/95 |
| 2,477,875 | 8/1949 | Hutchason | 222/95 |
| 2,490,303 | 12/1949 | Houck | 222/103 |
| 2,595,493 | 5/1952 | Slaby et al. | 141/24 |
| 2,687,727 | 8/1954 | Laushe | 604/212 |
| 2,815,895 | 12/1957 | Reed | 222/575 |
| 2,911,972 | 11/1959 | Elinger | 604/216 |
| 2,994,323 | 8/1961 | Dann et al. | 604/232 |
| 3,159,312 | 12/1964 | Van Sciver | 222/326 |
| 3,161,194 | 12/1964 | Chapman | 604/214 |
| 3,215,171 | 11/1965 | Mitchell | 604/216 |
| 3,223,289 | 12/1965 | Bouet | 222/95 |
| 3,272,401 | 9/1966 | Fendler et al. | 222/326 |
| 3,288,333 | 11/1966 | Valk | 222/326 |
| 3,323,682 | 6/1967 | Creighton et al. | 222/327 |
| 3,340,869 | 9/1967 | Bane | 222/215 |
| 4,040,420 | 8/1977 | Speer | 604/191 |
| 4,068,663 | 1/1978 | D'Alessandro | 604/212 |
| 4,131,217 | 12/1978 | Sandegren | 222/326 |
| 4,418,841 | 12/1983 | Eckstein | 222/107 |

FOREIGN PATENT DOCUMENTS

| | | | |
|---|---|---|---|
| 2294927 | 7/1976 | France | 222/95 |
| 1103917 | 2/1968 | United Kingdom | 604/214 |

Primary Examiner—H. Grant Skaggs
Attorney, Agent, or Firm—Browdy and Neimark

[57] ABSTRACT

A cartridge holds liquid, fluid or semi-fluid substances in tubes, and the cartridge is set in an extractor. The cartridge can all extract the charged substance, prevent it from flowing out, and extract the substance quantitatively.

Another embodiment of the cartridge is integrally provided with a needle so that it is applied as an injector, or to a container of holding a desired liquid or other extractor.

3 Claims, 2 Drawing Sheets

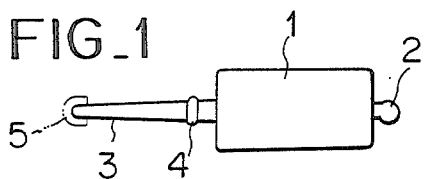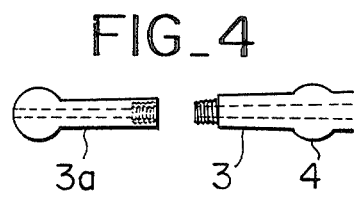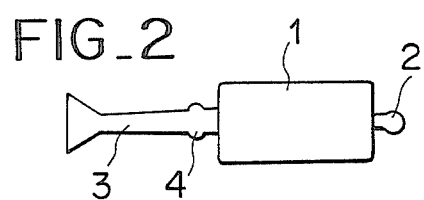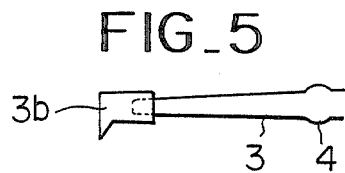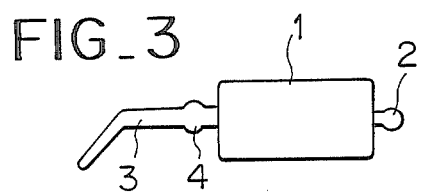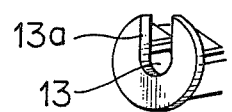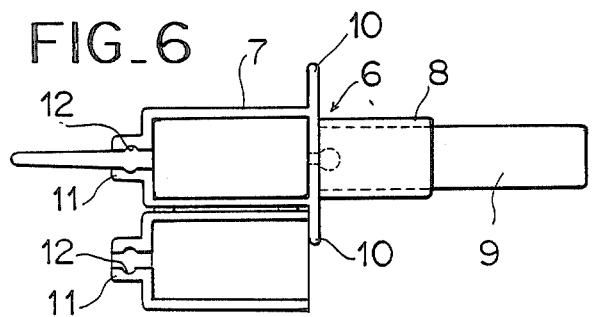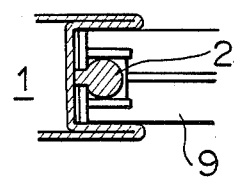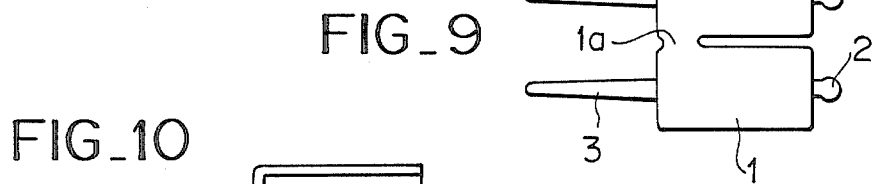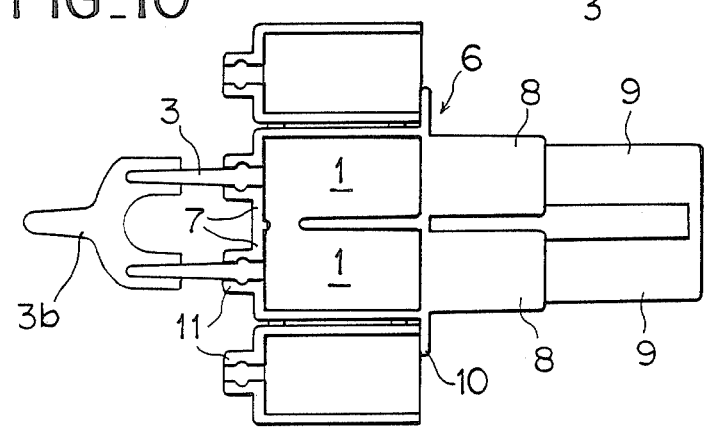

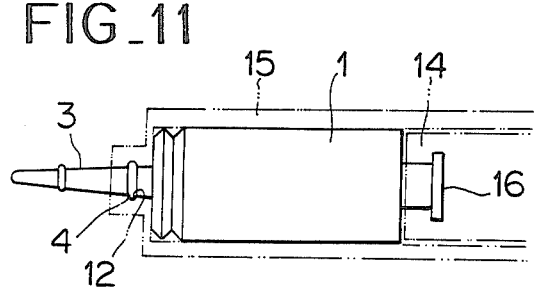
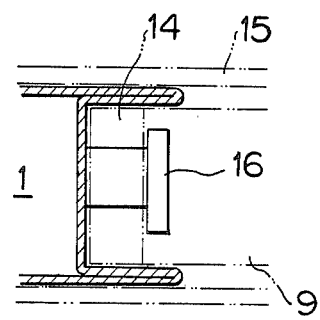
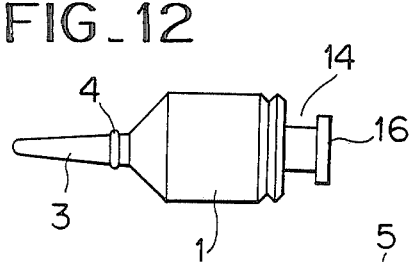
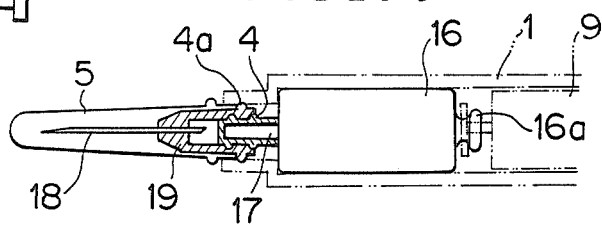
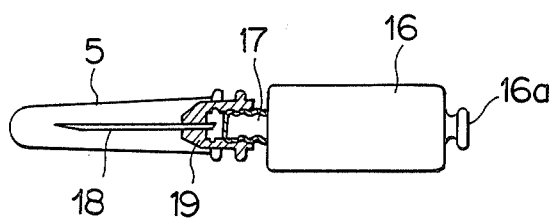
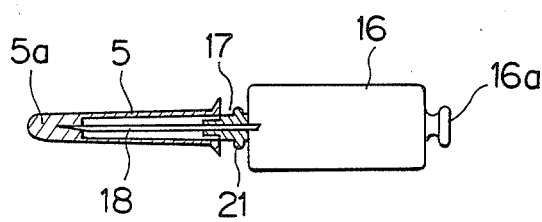
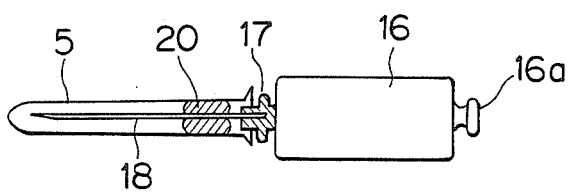
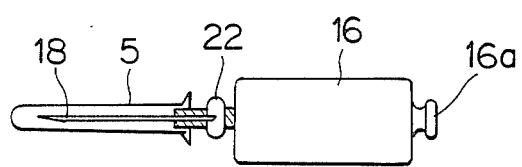

CARTRIDGE AND ITS EXTRACTOR

This is a continuation of parent application Ser. No. 704,883, filed Feb. 25, 1985, now abandoned in favor of the present application, and itself a continuation of earlier copending application Ser. No. 480,239, filed Mar. 29, 1983, abandoned in favor of parent application Ser. No. 704,883.

BRIEF DESCRIPTION OF THE INVENTION

This invention relates to a cartridge and its extractor, which holds liquid, or semi-fluid substances such as binding, plating or liquid agents, jelly-like contraceptive creams, and so on.

Many of said agents are provided in tubes, and they are squeezed out of the tubes by the use of one's fingers. The substance in the tube usually can not be all pressed out, or if a sealing cap is left off after use the agent may flow out due to inner pressure or changes in temperatures and it may become hard and dry about the tube mouth or dry on or about the cap.

Whereupon the present invention has been developed wherein the agent is filled into the cartridge and this cartridge is set in an extractor.

The invention is to provide a cartridge which can extract all the charged substance, prevent it from flowing out if the cartridge is left opened during use, extract quantitatively or jet the agent into the narrow space, and which can realize good economy because of the simple charging manner, and can use mixture of more than one agent.

The invention is to also provide a cartridge which is satisfactory in corrosion resistance and durability for holding binding or plating agents, and an extractor which can be repeatedly used by exchanging the cartridge.

The invention provides, as a further embodiment, a cartridge having a needle-like dispensing tip to be applied as an injector or to be inserted within a container. That is, this cartridge can be quickly dealt with at emergency or in the outdoors. The container can be repeatedly used by exchanging the cartridge only. If it is applied as the injector it could be quickly used without sterilization.

A primary object of the invention is that the cartridge made of a soft plastics is provided on its bottom with a fitting means for a piston of a presser and is extended with a injecting tube from its head.

A secondary structure of the invention arranges in parallel the cartridges as mentioned above.

In this regard, this kind of the cartridge is required to have following conditions:

(1) since the cartridge is set in the extractor and it is bent inwardly in double layers by pressing the bottom by means of a piston, it should have proper squeezing characteristics, (2) it has corrosion resistibility against the charged substance, (3) deformation caused by changing in temperatures is avoided by vapour tension of the solvent contained in the binding agent or other charged substance, (4) it has strength of more than 1 Kg/cm$^2$, (5) the charged material is prevented from flowing out.

The present invention is to provide a cartridge which satisfies all of these conditions.

The attached drawings illustrate embodiments of the invention.

BRIEF DESCRIPTION OF THE ATTACHED DRAWINGS

FIGS. 1 to 5 show different embodiments of the invention, respectively,

FIG. 6 is a view illustrating the cartridge attached within the extractor,

FIG. 7 is a view illustrating a fitting portion to be positioned at a front end of a piston, FIG. 8 is a view illustrating depression of the bottom of the cartridge, FIG. 9 is a second embodiment of the invention, FIG. 10 is a view illustrating the second embodiment attached within the extractor, FIGS. 11 and 12 are further embodiments which are different respectively, FIG. 13 is a vertical and cross sectional view showing depression of the pressed cartrdge, and FIGS. 14 to 18 are still further embodiments to be applied as injectors.

DETAILED DESCRIPTION OF PREFERRED EMBODIMENTS OF THE INVENTION

An explanation will be made to a first embodiment of the invention shown in FIGS. 1 to 5. A container cartridge 1 made of soft plastic is filled with a binding agent, a plating agent, liquid medicine, jelly-like contraceptive or so on. The container 1 has, on its bottom, a means for engaging a piston 9 (see FIGS. 6-8) of an extractor, and one such engaging means shown with a reference numeral 2 is a projection. The projection 2 is engaged at a front end portion of a piston 9 as later mentioned, and any shape is sufficient for the projection 2. A needle-like dispensing tip or injecting tube 3 extends from the front part of the cartridge container 1 and is formed with an engaging means 4 for engaging with the extractor. One such engaging means is a convex bead 4 which fits in a concave recess 12 defined within the extractor, thereby to secure the cartridge therewithin. A cap 5 is provided to prevent the substance from flowing out.

Many variations may be assumed for the injecting tube 3. For example, the end portion may be shaped in spatula form for wide starching (FIG. 2), bending for curved parts (FIG. 3), or ball form for injecting e.g. jelly-like contraceptive (FIG. 4), or it may be devised for atomization. Further the injecting tube 3 may be made bendable and lengthy for reaching through a narrow and bending path, or otherwise the tube 3 may be formed of hard plastic so as not to bend. The tube 3 may be exchangeable at its middle portion (FIG. 4), and for this case several kinds of attachments 3a are prepared in view of using distinations. The attachment depends upon mounting or screwing types. The attachment may be for an end portion only (FIG. 5). Preferably, the cartridge container may have bellows, too.

FIG. 6 shows that the cartridge is placed within the extractor 6. The extractor 6 which is formed of two semi-cylindrical halves hinged together comprises a cartridge supporting part 7 of size and shape to receive and support the cartridge, a piston inserting portion 8 continuing therefrom of about the same internal cross-section, and a piston 9. The cartridge supporting part 7 is formed with finger supports 10,10 and projections 11,11 defining the concave recess 12 for interfitting with the convex bead 4 of the tube 3. The convex bead 4 and the concave 12 may reversely arranged. There will be a type where the cartridge is inserted at a rear side, and in this case, for example, the cartridge is inserted and turned half rotation such that it is secured in the extractor. The projection 2 of the cartridge container 1 is held at the front end portion of the piston 9 by e.g. defining a vertical groove 13 for fitting the projection 2 at the front end portion of the piston 9, mounting the projection 2 upwardly thereinto, and catching it between edges 13a of the groove 13 (FIGS. 7 and 8). The holding means is not limited to such a system, and various ways will appear in mind. FIG. 8 for example illustrates a pressing condition of the cartridge.

A next reference will be made to an embodiment shown in FIGS. 9 and 10. The present embodiment arranges in parallel a plurality of the cartridges having been referred to up to now (shown ones are two cartridges). The containers are ordinarily combined at a part 1a (FIG. 9). This is for mixing two liquid agents, and FIG. 10 shows that the multi-cartridges are attached into a new extractor 6. In the present case, the pistons 9 are combined, but those are separated if the cartridges are to be pressed individually. If it is preferable to mix the agents before injecting, the injecting mouths at the ends of the tubes 3 are connected. This connection may be effected via a connecting attachment 3b as shown in FIG. 10.

The use of the invention will be explained with respect to the embodiments. In the first embodiment, the cartridge supporting part 7 of the extractor 6 is opened and the cartridge is placed therein, and the convex bead 4 is fitted into the concave grooves 12 while the projection 2 is set into the vertical groove 13 of the piston 9. Then, the cartridge supporting part 7 is closed, and the fingers hold the finger supports 10, and the discharge end portion of the tube 3 is directed to an object, and the piston 9 is pressed by a thumb. The soft and flexible cartridge is pressed at its bottom, and it is depressed and everted into a double thickness; as shown in FIG. 8 (or the container cartridge in the bellows form is shrunk in folding), and the contained material is driven out the injecting tube 3 which is selected in shape in accordance with usage, using positions and others.

If the piston 9 is withdrawn a little, the bottom of the cartridge is also returned so that the filled material within the injecting tube 3 flows backward due to negative pressure within the cartridge. Consequently, the liquid contents do not stay within the injecting tube 3 nor flow out by the inner pressure or changes in temperatures. Since the convex bead 4 is fitted in the concave grooves 12, the entire body of the cartridge is not pulled and moved, but its bottom only is squeezed and everted.

With respect to the second embodiment shown in FIGS. 9 and 10, the two agents are pressed out simultaneously by pushing the combined piston 9. When the injecting tubes 3 are connected via the attachment 3b, the mixed agents are injected.

A still further embodiment according to the invention will be explained with reference to FIGS. 11 to 13. A cartridge shown in FIG. 11 comprises a container 1 for holding the liquid substance such as the binding or plating agents, an injecting tube 3 extending from the cartridge container 1 and a mouth 14 for filling the liquid agent. The container 1 is formed with a bellows at its front part, only one bellows being illustrated. The cartridge is formed with triple structure of polyethylene, high barrier resin and polyethylene. Polyethylene of the inner and outer layers is blended with binding modified polymer (since polyethylene homopolymer is not combined with high barrier resin, it is blended with binding modified polymer), and each of the layers is made e.g. 100 micron in thickness. For high barrier resin, nylon or vinyleden chloride may be used, but preferably Eval (reg. T.M. of polyethylene modified polymer manufactured by Kurera). The high barrier layer should be controlled around 50 micron thickness in view of the required squeezing property. A ring-like projection 4 is for fitting in a circumferential groove 6 defined on a neck portion of an extractor 15. The ring-like projection 4 serves to fix the cartridge during pumping. The filling mouth 14 is provided with a flange 16 for holding an end portion of a piston 9 of the extractor 15.

FIG. 12 shows another cartridge which is for containing a liquid substance of low viscosity. Since this case does not necessarily require the squeezing property, a middle layer of high barrier resin could be relatively thick. For example, the inner and outer polyethylene layers are made 50 micron and the middle high barrier layer is made 100 microns thick. The charging mouth 14 is sealed with a cap which is preferably made of high barrier resin. The sealing should depend upon a supersonic sealing process, whereby if the binding agent adheres the mouth 14, the sealing is possible and satisfactory in strength and leakage prevention.

Another reference will be made to a cartridge with a needle. The cartridge 16 is provided with a needle 18 at a neck portion 17. FIGS. 14 to 18 show different conditions of needle attachments. In FIG. 14, the neck portion 17 is formed on its circumference with a plurality of projections 4, and is mounted with a needle fixing member 19 which is defined with grooves to be fitted on the projections 4. The numeral 5 is a sterilized cap, 1 is a container and 9 is a piston. In this embodiment, the cartridge 16 is housed in the container 1, and the needle fixing member 19 is inserted with the fingers. Then, preceding projections 4 are mounted in the circumferential groove of the needle fixing member 19, and the rear end of the needle 18 pierces a front end of the neck portion 17. If the cap 5 is removed and the piston 9 is urged, a medicine liquid is pressed out along the needle 3. The numeral 16a is an engaging portion provided on the bottom of the cartridge 16 for catching an engaging portion provided on the front part of the piston 9. These engaging portions and a means of checking movement of the cartridge serve for pumping action.

In an embodiment shown in FIG. 15, a surface of the neck portion 17 of the cartridge 16 and the inner surface of the needle fixing member 19 are formed with screws for screwing both together.

An embodiment shown in FIG. 16 has in advance pierced the needle 18 into the neck portion toward the cartridge 16, and in this case a soft sealing portion 5a within the cap 5 is prepared so that the needle 18 runs into this soft sealing portion 5a to prevent leakage. The numeral 21 is an engaging ring which corresponds to the projection 4 in the first embodiment.

With respect to an embodiment shown in FIG. 17, the needle 18 is caught in the neck portion 17 at its rear end, and a minor member 20 is fixed on the needle 18. For use, the minor member 20 is held on the sterilized cap 6, so that the needle 18 goes into the neck portion 2.

In an embodiment shown in FIG. 18, the neck portion 17 is provided with an air stay 22 which catches the needle at its rear portion. For use, if the neck portion 17 is pressed together with the sterilized cap 5, the air stay 22 is crashed and the needle 18 pierces through the neck portion 17.

What is claimed is:

1. An injection apparatus for discharging liquid carried within a container, said apparatus comprising:
   a cartridge including said container prefilled with said liquid, an injecting tube formed integrally with said container and extending in a forward, discharging direction from said container, and a projection means integrally formed with said container and extending in a rearward direction, said container being collapsible in said discharging direction;
   a housing for supporting said cartridge; and
   a piston, supported by a rearward portion of said housing, for reversible sliding motion relative to said cartridge, said piston including a forward portion including means for coupling said cartridge projection means with said piston forward end,
   said housing comprising a hollow portion for supporting said container, and a projection extending forwardly from said hollow portion, said projection including a bore extending therethrough for supporting the injecting tube of said cartridge, said projection including a recess disposed in the wall of said bore and extending in a direction generally normal to the discharging direction, said injecting tube having a forward portion extending forwardly and outside of said projection, and a rearward portion having convex projection extending in said generally normal direction, said injecting tube convex projection cooperating with said projection bore wall recess to secure said cartridge in a fixed position relative to said housing;
   wherein said housing comprises shell-like sections, and means for joining said sections, whereby the cartridge may be disposed in one of said housing sections by first inserting the cartridge rearward end into the rearward portion of said one housing section, and then placing the container and injecting tube of said cartridge in the one housing section hollow portion and projection, respectively,
   wherein said container comprises two receptacles each carrying a liquid, and each having an injection tube and projection means, said receptacles being disposed in parallel relationship and being joined to each other at their adjacent sides,
   said housing comprises three of said sections including a base section and two cover sections, said base section being disposed between said cover sections and having a hollow portion configured to support said two receptacles, and
   said piston comprises two parallel plungers, each of said plungers having a forward end and a rearward end, the forward end of each of said plungers being coupled with the projection means of a respective receptacle, and the rearward ends of said plungers being joined to one another,
   whereby movement of said piston in said discharging direction causes simultaneous discharge of the liquids from said receptacles through respective injecting tubes.

2. The injection apparatus of claim 1, further comprising tubular means for mixing the liquids after their discharge from said injecting means.

3. An injection apparatus for discharging a flowable material, comprising:
   a closed cartridge formed of a flexible material having a uniform wall thickness and filled with said flowable material, an injecting tube formed integrally at a front end of said closed cartridge and extending in a forward discharging direction, a first coupling means integrally formed at a rear end of said closed cartridge and extending in a rearward direction, said cartridge being collapsible from said rear end in said discharging direction and evertable at said rear end;
   an extractor housing having a first forward portion for cylindrically and forwardly supporting and fully circumferentially enclosing said closed cartridge, said extractor housing having an internal configuration complimentary to the external configuration of said cartridge, said housing having a rearwardly extending second portion for slidably supporting a piston, said first portion being formed of two semi-cylindrical sections; and second portion being formed as a circumferentially closed cylinder;
   a piston, supported by said second portion of said extractor housing, for reversibly sliding motion relative to said closed cartridge, said piston having a forward portion including a second coupling means for coupling to said first coupling means so as to connect said rear end of cartridge with said piston forward end;
   said extractor housing having a forwardly extending projection including a bore extending therethrough for circumferentially supporting the injecting tube of said cartridge, said projection including a recess disposed in the wall of said bore and extending in a direction generally normal to the discharging direction, said injecting tube having a forward portion extending beyond said projection and a rearward portion having a convex bead extending in said generally normal direction, said injecting tube convex bead cooperating with said projection bore recess to secure said cartridge in a fixed position within said extractor housing.

* * * * *